United States Patent [19]

Martel et al.

[11] 4,111,994
[45] Sep. 5, 1978

[54] PREPARATION OF OPTICALLY ACTIVE ALLETHROLONE

[75] Inventors: Jacques Martel, Bondy; Jean Tessier, Vincennes, both of France

[73] Assignee: Roussel Uclaf, Paris, France

[21] Appl. No.: 820,096

[22] Filed: Jul. 29, 1977

[30] Foreign Application Priority Data

Aug. 26, 1976 [FR] France ................ 76 25799

[51] Int. Cl.² ........................... C07C 45/24
[52] U.S. Cl. ............................... 260/586 R
[58] Field of Search ..................... 260/586 R

[56] References Cited

U.S. PATENT DOCUMENTS

| | | | |
|---|---|---|---|
| 2,891,888 | 6/1959 | Guest et al. | 260/586 R |
| 3,720,703 | 3/1973 | Elliot et al. | 260/586 R |
| 4,005,146 | 1/1977 | Goffmet | 260/586 R |

OTHER PUBLICATIONS

La Forge et al., "J. Org. Chem.," 19,457 (1954).
La Forge et al., "J.A.C.S." 74 (1952) p. 5392.

Primary Examiner—Norman Morgenstern
Attorney, Agent, or Firm—Hammond & Littell

[57] ABSTRACT

A process for the preparation of optically active allethrolone of (S) or (R) configuration comprising reacting in at least one organic solvent a sulfonate of optically active allethrolone of (R) or (S) configuration of the formula

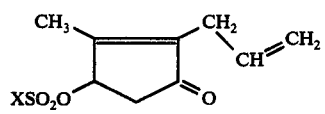

wherein X is selected from the group consisting of alkyl of 1 to 3 carbon atoms and phenyl optionally substituted in the p-position with a member of the group consisting of methyl, chlorine, bromine and fluorine with a salt of an organic carboxylic acid selected from the group consisting of aliphatic carboxylic acids of 1 to 6 carbon atoms optionally substituted with one or more halogens and a monocyclic aromatic carboxylic acid to form the ester of the carboxylic acid and (S) or (R) allethrolone antipodal to that of the starting sulfonate of allethrolone and subjecting the latter to acid hydrolysis to form (S) or (R) allethrolone antipodal to the starting sulfonate which allethrolones form insecticidally active esters with cyclopropane carboxylic acids.

5 Claims, No Drawings

PREPARATION OF OPTICALLY ACTIVE ALLETHROLONE

STATE OF THE ART

French Pat. No. 2,166,503 discloses the resolution of racemic allethrolone to obtain (S) allethrolone whose cyclopropane carboxylic acid esters have, in general, a more elevated insecticidal activity than the corresponding cyclopropane carboxylic acid esters of (R) allethrolone. Therefore, it is very useful industrially to transform optically active (R) allethrolone into optically active (S) allethrolone because its esters are much more insecticidally active.

In commonly assigned U.S. patent application Ser. No. 795,021 filed May 9, 1977, there is described a process for the racemization of (R) allethrolone and commonly assigned U.S. patent application Ser. No. 807,069 filed June 16, 1977 describes a process for direct transformation of (R) allethrolone into (S) allethrolone by hydrolysis in a basic medium of a sulfonate of (R) allethrolone.

OBJECTS OF THE INVENTION

It is an object of the invention to provide a novel process for transforming an optically active isomer of allethrolone into allethrolone of antipodal configuration.

It is another object of the invention to provide a novel process for transforming (R) allethrolone into (S) allethrolone.

These and other objects and advantages of the invention will become obvious from the following detailed description.

THE INVENTION

The novel process of the invention for preparing optically active allethrolone of (S) or (R) configuration comprises reacting in at least one organic solvent a sulfonate of optically active allethrolone of (R) or (S) configuration of the formula

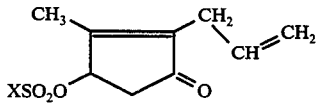

wherein X is selected from the group consisting of alkyl of 1 to 3 carbon atoms and phenyl optionally substituted in the p-position with a member of the group consisting of methyl, chlorine, bromine and fluorine with a salt of an organic carboxylic acid selected from the group consisting of aliphatic carboxylic acids of 1 to 6 carbon atoms optionally substituted with one or more halogens and a monocyclic aromatic carboxylic acid to form the ester of the carboxylic acid and (S) or (R) allethrolone antipodal to that of the starting sulfonate of allethrolone and subjecting the latter to acid hydrolysis to form (S) or (R) allethrolone antipodal to the starting sulfonate. This process will be designated α.

Examples of sulfonates of the optically active allethrolone are those wherein X is methyl, ethyl, p-tolyl, p-chlorophenyl and p-bromophenyl, particularly the methane sulfonate or p-toluene sulfonate.

Examples of suitable carboxylic acids whose salts are useful in the process are lower alkanoic and alkanedioic acids optionally halogenated such as acetic acid, chloroacetic acid, dichloroacetic acid, butyric acid, isobutyric acid, straight or branched chain pentanoic acid, ω-dichlorobutyric acid, oxalic acid, succinic acid, etc. and aromatic carboxylic acids such as phthalic acid. Preferred acids are dichloroacetic acid, chloroacetic acid, acetic acid, oxalic acid, isobutyric acid, pathalic acid and succinic acid and most preferably dichloroacetic acid.

The salts of the carboxylic acid may be alkali metal, alkaline earth metal and ammonium salts and salts of a tertiary base such as tertiary amines. The preferred salts are the sodium and potassium salts. When the acid used is a dicarboxylic acid, preferably only one of the acid groups is salified to obtain generally besides the hemiester of the antipodal allethrolone a preponderant quantity of the diester of the antipodal allethrolone. Both of the said esters may be hydrolyzed to the desired antipodal allethrolone.

The organic solvent for the said reaction may be, for example, dimethylformamide, dimethylsulfoxide, dimethoxyethane, acetonitrile, aliphatic ketones, hexamethylphosphortriamide, alkanols, monocyclic aromatic hydrocarbons and mixtures thereof. Preferred solvents are dimethylformamide, dimethylsulfoxide, hexamethylphosphortriamide, tertiary butanol and mixtures of toluene and tertiary butanol.

The sulfonates of optically active allethrolone may be prepared by reacting the sulfonyl chloride with optically active allethrolone in a solvent selected from the group consisting of aliphatic ketones of 3 to 6 carbon atoms, monocyclic aromatic hydrocarbons, ether oxides and chlorinated solvents and preferably the sulfonate of allethrolone is not recovered from the reaction medium in which it is prepared. The preferred solvent is an aromatic hydrocarbon.

The preparation of the salt of the carboxylic acid is effected in a solvent or mixture of solvents selected from the group consisting of dimethylformamide, dimethylsulfoxide, dimethoxy-ethane, acetonitrile, aliphatic ketones, hexamethylphosphortriamide, alkanols, monocyclic aromatic hydrocarbons and mixtures thereof and the salts are preferably not isolated from the reaction medium.

The acid agent for the hydrolysis of the ester of the carboxylic acid ester of optically active allethrolone is preferably a strong acid in dilute solution, most preferably dilute hydrochloric acid solution or dilute sulfuric acid solution.

In a preferred mode of the invention to prepare (S) or (R) allethrolone, the methane sulfonate of (R) or (S) allethrolone is reacted with sodium dichloroacetate to obtain the dichloroacetate of optically active allethrolone antipodal to the configuration of the starting allethrolone and subjecting the latter to hydrolysis by heating in an aqueous 2N hydrochloric acid solution to obtain optically active allethrolone antipodal to the starting product. The process of the invention is particularly interesting for preparing (S) allethrolone from (R) allethrolone by starting with a sulfonate of (R) allethrolone.

The process of the invention presents a stage wherein the process consists of saponifying a sulfonate of allethrolone offering the advantage of leading, in practice, to an elevated yield of the transformation of (R) allethrolone into (S) allethrolone. In effect, in the process of the invention, the inversion of the center of asymmetry of allethrolonne is effected by action of the salt of the carboxylic acid on the sulfonate of allethrolone and this type of basic agent has proved to be particularly convenient to effect the inversion. This use permits avoidance or at least considerably limits side reactions which can take place in the presence of a basic agent and which are most troublesome when effecting direct inversion of a sulfonate of allethrolone. The final acid hydrolysis of the carboxylate of the inverted allethrolone, especially under the preferred conditions of the process of the invention, also permit maximum avoidance of secondary reactions which would be feared in an acid media.

The process of the invention permits the transformation of (R) allethrolone to (S) allethrolone in high yields under conditions easily industrialized.

However, the resolution of racemic allethrolone is not effected in 100% yields furnishing in practice besides (S) allethrolone, a mixture of (R) and (S) allethrolone rich in (R) allethrolone. The said mixture may be reacted with a sulfonyl chloride to form a mixture of the sulfonates of (R) and (S) allethrolone which can also be used as a starting material for the process of the invention.

The sulfonates of allethrolone of formula I are described in U.S. patent application Ser. No. 807,069 referred to above by reacting in an organic solvent or mixture of organic solvents in the presence of a basic agent a sulfonic acid chloride of the formula XSO$_2$Cl     II where X has the above definition with (R) or (S) allethrolone or mixtures thereof. The basic agent is preferably a tertiary base, especially triethylamine and the organic solvent may be aliphatic ketones of 3 to 6 carbon atoms, monocyclic aromatic hydrocarbons, ether oxides, chlorinated solvents or mixtures thereof. The preferred solvents are toluene or acetone and the sulfonic acid chlorides are preferably methane sulfonyl chloride or p-toluene sulfonyl chloride.

The process of the invention has the unexpected character in that allethrolone presents, in effect, a very special structure of cyclic allylic alcohol which has a 2,3-double bond in the ring which activates the alcoholic hydroxyl and a ketone group which activates the hydrogen γ of the alcohol function. While at first place it might appear easy, the preparation of sulfonates of allethrolone has serious difficulties because of the special reactivity of the alcohol.

Such a structure is known to be fragile in a basic medium as discussed by LaForge [J.A.C.S., Vol. 74 (1952), p. 5392] and it was to be feared, a priori, that the action of a basic agent with a methane sulfonate of allethrolone would give rise to secondary reactions such as leading by the Diels-Alder reaction to dimers of allethrolone of the formulae

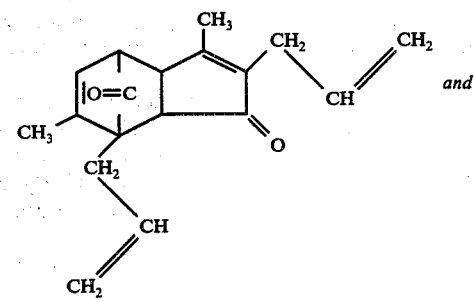

and

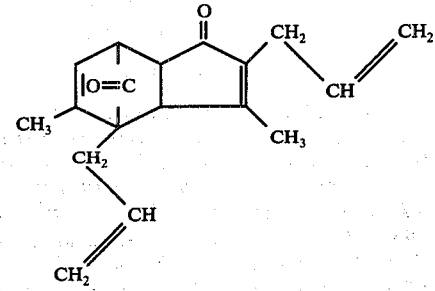

-continued

On the contrary, it has been found that the salts of the carboxylic acids used in the invention and especially the salts of strong bases with the acids do not lead to secondary reactions so that elevated yields of the carboxylic acid ester of allethrolone antipodal to the starting allethrolone are obtained.

In the final hydrolysis in acid media of the carboxylate of allethrolone, there was equally the fear of secondary reactions due to easy protonation of the allylic alcoholic oxygen of allethrolone which is particularly reactive and could lead to a reaction of the following type

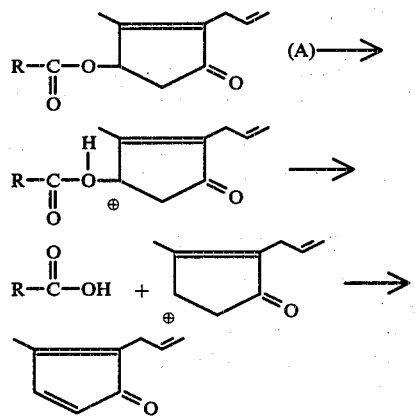

leading to a dienic compound which is very reactive.

The use of the preferred mode of dilute solutions of strong acids permits avoidance of this type of parasitic reaction. Finally, in spite of the great reactivity of allethrolone as well in basic and acid media which permitted fears of defeat in practice of an inversion method using basic and acid agents, the process of the invention has surprisingly led to high yields of an antipodal allethrolone of good purity.

In the following examples there are described several preferred embodiments to illustrate the invention. However, it should be understood that the invention is not intended to be limited to the specific embodiments.

EXAMPLE 1

STEP A: methane sulfonate of (R) allethrolone 8.8 ml of triethylamine were added at −15° C to a solution of 7.6 g of (R) allethrolone with a specific rotation $[\alpha]_D^{20} = -15° \pm 1°$ (c = 1% in chloroform) containing 97.5% of (R) allethrolone and 2.5% of (S) allethrolone according to circular dichroism in 15 ml of acetone and then a solution of 6.6 g of methane sulfonyl chloride in 5 ml of acetone was slowly added thereto with stirring. The mixture was stirred at −10° C for 1 hour and was then poured into a mixture of water, N hydrochloric acid and methylene chloride. The mixture was stirred at room temperature and the organic phase was decanted. The aqueous phase was extracted again with methylene chloride and the combined organic phases were dried over sodium sulfate and evaporated to dryness to obtain 11.6g of raw methane sulfonate of (R) allethrolone which was used as is for the next step.

STEP B: Dichloroacetate of (S) allethrolone

A few crystals of phenolphthalein were added to a solution of 38.8 g of dichloroacetic acid in 100 ml of methanol and 2N sodium hydroxide was added until the end point of the indicator. The mixture was then evaporated to dryness under reduced pressure and the residue was ground in a homogenizer and was added to benzene. The benzene was distilled to obtain 46 g of raw sodium dichloroacetate which was used as is.

The 11.6 g of product of Step A were added to a solution of 8.3 g of sodium dichloroacetate in 35 ml of hexamethyl-phosphortriamide and the mixture was stirred for one hour. 40 ml of water were added thereto and the mixture was extracted with petroleum ether. The combined organic extracts were dried and evaporated to dryness to obtain 12.23 g of raw dichloroacetate of (S) allethrolone which was used as in for the next step.

STEP C: (S) allethrolone

The product of Step B was added to 60 ml of aqueous 2N hydrochloric acid and the mixture was refluxed for 5 hours and was then cooled. Water was added to the mixture which was then extracted with petroleum ether. The aqueous phase was made alkaline by the slow addition of 60 ml of 2N sodium hydroxide and then with sodium bicarbonate to obtain a pH of 8-9. The solution was saturated with sodium chloride and was extracted with methylene chloride. The combined organic phases were dried and evaporated to dryness under reduced pressure to obtain 6.42 g of (S) allethrolone with a specific rotation of $[\alpha]_D^{20} = 12.5° \pm 1°$ (c = 1% in chloroform).

Circular Dichroism (dioxane):

Infl. at 345 nm $\Delta^\epsilon = +1.23$
Max. at 331 nm $\Delta^\epsilon = +2.51$
Max. at 321 nm $\Delta^\epsilon = +2.74$
Infl. at 310 nm $\Delta^\epsilon = +2.09$
Max. at 230 nm $\Delta^\epsilon = -19.1$ U.V. Spectrum (ethanol):

Max. 230 nm $E_1^1 = 791$ $\epsilon = 12,000$
Infl. 275 nm $E_1^1 = 6$
Infl. 300 nm $E_1^1 = 5$ From the circular dichroism, it was ascertained that the allethrolone was 92.5% (S) allethrolone and 7.5% (R) allethrolone.

EXAMPLE 2

6.85 g of methane sulfonyl chloride were slowly added at −13° C to a solution of 7.6 g of (R) allethrolone in 23 ml of toluene and then a solution of 6.7 g of methylamine in 6.5 ml of toluene was added thereto over 2 hours at −10° C. The mixture was stirred for 15 minutes and 30 ml of water were added over 30 minutes at −5° C. The mixture was stirred and the organic phase was decanted. The aqueous phase was extracted with toluene and the combined toluene phases were dried and evaporated to dryness under reduced pressure to obtain 11.6 g of raw methane sulfonate of (R) allethrolone.

In a modification of the process, 9.7 ml of triethylamine were added at −6° C to a solution of 7.6 g of (R) allethrolone in 90 ml of a 1-1 benzene-ether mixture and then a solution of 4 ml of methane sulfonyl chloride in 54 ml of a 1-1 benzene-ether mixture was slowly added thereto. The mixture was stirred for 3 hours at −10° C and was then poured into a dilute hydrochloric acid solution. The organic phase was decanted and the aqueous phase was extracted with ether. The combined organic phases were washed with water, dried and evaporated to dryness under reduced pressure to obtain 11.5 g of methane sulfonate of (R) allethrolone.

EXAMPLE 3

STEP A: p-toluene sulfonate of (R) allethrolone 11.6 g of triethylamine and then 21.9 g of p-toluene sulfonyl chloride were added at −50° C under an inert atmosphere to a mixture of 11.6 g of (R) allethrolone in 100 ml of tetrahydrofuran and the mixture was stirred for 48 hours at 5° C after which it was poured with stirring into aqueous 0.1N hydrochloric acid solution. The aqueous phase was extracted with chloroform and the organic extracts were washed with water, dried and evaporated to dryness. The 29 g of residue was chromatographed over silica gel and was eluted with a 95-5 benzene-ethyl acetate mixture to obtain 6.8 g of p-toluene sulfonate of (R) allethrolone.

STEP B: dichloroacetate of (S) allethrolone

A solution of 1.4 g of the product of Step A in 5 ml of hexamethylphosphortriamide was progressively added to a mmixture of 0.750 g of sodium dichloroacetate in 10 ml of hexamethylphosphortriamide and the mixture was stirred at 20° C for 6 hours. Water was added thereto and the mixture was extracted with petroleum ether (b.p. = 35°–75° C). The organic extracts were washed with water, dried and evaporated to dryness to obtain 1.033 g of raw dichloroacetate of (S) allethrolone which was used as is for the next step.

STEP C: (S) allethrolone

A mixture of the product of Step B in 5 ml of aqueous 2N hydrochloric acid was heated at 90°–95° C for 5 hours and was then cooled and water was added thereto. The mixture was neutralized with sodium bicarbonate and was saturated with sodium chloride. The mixture was extracted with chloroform and the extracts were dried and evaporated to dryness. The 0.592 g of residue was chromatographed over silica gel and was eluted with a 7-3 benzene-ethyl acetate mixture to obtain 0.358 g of (S) allethrolone.

EXAMPLE 4

STEP A: methane sulfonate of (S) allethrolone 8.8 ml of triethylamine were slowly added at −15° C to a solution of 7.6 g of (S) allethrolone with a specific rotation of $[\alpha]_D^{20} = 15°$ (c = 1% in chloroform) in 23 ml of toluene and a solution of 6.6 g of methane sulfonyl chloride in 5 ml of acetone was slowly added thereto with stirring. The mixture was stirred for 1 hour at −10° C and was then poured into a mixture of water, methylene chloride and N hydrochloric acid. The mixture was stirred at room temperature and the organic phase was decanted. The aqueous phase was extracted again with methylene chloride and the combined organic phases were dried over sodium sulfate and concentrated to dryness to obtain 11.6 g of methane sulfonate of (S) allethrolone.

STEP B: monochloracetate of (R) allethrolone

A solution of 5.75 g of methane sulfonate of (S) allethrolone in 10 ml of hexamethylphosphortriamide was added under an inert atmosphere to a mixture of 3.5 g of potassium monochloracetate in 30 ml of hexamethylphosphortriamide and the mixture was stirred at 25° C for 15 hours. The mixture was poured into water and was extracted with petroleum ether (b.p. =35°-75° C). The organic extracts were washed with water, dried and evaporated to dryness to obtain 3.90 g of raw monochloracetate of (R) allethrolone.

STEP C: (R) allethrolone

A mixture of the product of Step B in 20 ml of aqueous 2N hydrochloric acid was refluxed for 5 hours and was then cooled and poured into water. The mixture was extracted with petroleum ether (b.p. = 35-75° C) and the aqueous phase was adjusted to a pH of 7 with aqueous sodium hydroxide solution. The mixture was saturated with sodium chloride and was extracted with methylene chloride. The methylene chloride extracts were washed with water, dried and concentrated to dryness to obtain 1.75 g of (R) allethrolone.

Using the same process, the methane sulfonate of (R) allethrolone was converted into (S) allethrolone with the same yield.

EXAMPLE 5

STEP A: acetate of (R) allethrolone

A solution of 14.7 g of methane sulfonate of (S) allethrolone in 16 ml of hexamethylphosphortriamide was added under an inert atmosphere to a mixture of 5.35 g of sodium acetate in 40 ml of hexamethylphosphortriamide and the mixture was stirred at 25° C for 15 hours and was then poured into water. The pH of the mixture was adjusted to 9.5 by addition of sodium bicarbonate and the aqueous phase was then extracted with petroleum ether (b.p. = 35°-75° C). The combined organic phases were washed with water, dried and evaporated to dryness. The residue was rectified under reduced pressure to obtain 8.55 g of raw acetate of (R) allethrolone with a boiling point of 88°-92° C at 0.7mm Hg.

STEP B: (R) allethrolone

A mixture of the raw product of Step A in 43 ml of 2N aqueous hydrochloric acid was refluxed for 2 hours and the mixture was ccooled and poured into an aqueous solution saturated with sodium bicarbonate.. The mixture was cooled to 5° C and the aqueous phase was saturated with sodium chloride. The mixture was extracted with methylene chloride and the extracts were dried and evaporated to dryness to obtain 6.15 g of (R) allethrolone.

Using an analogous process, the methane sulfonate of (R) allethrolone was converted to (S) allethrolone in the same yields.

EXAMPLE 6

STEP A: isobutyrate of (R) allethrolone

A solution of 23 g of the methane sulfonate of (S) allethrolone in 30 ml of hexamethylphosphortriamide was progressively added under an inert atmosphere to a mixture of 11.5 g of sodium isobutyrate in 80 ml of hexamethylphosphortriamide and the mixture was stirred for 20 hours at 25° C. The mixture was poured into water and the pH was adjusted to 9.5 with sodium bicarbonate. The mixture was extracted with petroleum ether (b.p. = 35°-75° C) and the extracts were dried and evaporated to dryness to obtain a residue containing isobutyrate of (R) allethrolone.

STEP B: (R) allethrolone

The raw residue of Step A in 60 ml of aqueous 2N hydrochloric acid was refluxed for 3 hours and was then cooled and poured into water. The mixture was extracted with petroleum ether (b.p. = 35°-75° C) and the pH of the aqueous phase was adjusted to 7 with aqueous sodium hydroxide solution. The mixture was saturated with sodium chloride and was extracted with methylene chloride. The organic extracts were dried and concentrated to dryness to obtain 7.6 g of (R) allethrolone.

Using an analogous procedure, the methane sulfonate of (R) allethrolone was converted to (S) allethrolone in the same yields.

EXAMPLE 7

STEP A: hemioxalate of (R) allethrolone and oxalate of di-(R)-allethrolone 11.5 g of the methane sulfonate of (S) allethrolone were progressively added under an inert atmosphere to a mixture of 5.6 g of anhydrous sodium hemioxalate in 30 ml of a hexamethylphosphortriamide and the mixture was heated at 80° C for 4 hours and was then cooled. The mixture was poured into water and the pH was adjusted to 9.5 with sodium bicarbonate. The mixture was vacuum filtered and the recovered precipitate was washed with petroleum ether (b.p. = 35°-75° C) to obtain 5.8 g of oxalate of di-(R)-allethrolone. The pH of the aqueous phase was adjusted to 1 and the aqueous phase was saturated with ammonium chloride and was extracted with ether. The ether extracts were evaporated to dryness to obtain 1.6 g of the hemioxalate of (R) allethrolone.

STEP B: (R) allethrolone

A mixture of 1.6 g of the hemioxalate of Step A in 8 ml of aqueous 2N hydrochloric acid was refluxed and the mixture was cooled and was extracted with petroleum ether. The aqueous phase was neutralized with sodium carbonate and was saturated with sodium chloride. The mixture was extracted with methylene chloride and the organic extracts were dried and evaporated to dryness to obtain 0.68 g of (R) allethrolone.

A mixture of 5.8 g of the oxalate of Step A in 30 ml of aqueous 2N hydrochloric acid was refluxed for 5 hours and was treated as above to obtain 4.54 g of (R) allethrolone.

Using an analogous procedure, the methane sulfonate of (R) allethrolone was converted to (S) allethrolone in the same yields.

EXAMPLE 8

STEP A: hemiphthalate of (R) allethrolone

A solution of 7.36 g of the methane sulfonate of (S) allethrolone in 8 ml of hexamethylphosphortriamide was added over 30 minutes under an inert atmosphere to a solution of 6.02 g of sodium hemiphthalate in 25 ml of hexamethylphosphortriamide and the solution was stirred at 25° C for 15 hours. The mixture was poured into water and was then extracted with petroleum ether (b.p. = 35°–75° C). The organic extracts were dried and filtered to obtain 2.85 g of a complex residue containing 2.1 g of phthalate of di-(R)-allethrolone. The aqueous phase was extracted with chloroform to remove excess hexamethylphosphortriamide and was cooled to 5° C and was acidified to a pH of 1. The mixture was extracted with chloroform and the extracts were evaporated to dryness to obtain 5.53 g of raw hemiphthalate of (R) allethrolone.

STEP B: (R) allethrolone

The hemiphthalate and phthalate products of Step A were then subjected to hydrolysis with aqueous 2N hydrochloric acid as in Step B of Example 7 to obtain (R) allethrolone. Using an analogous process, the methane sulfonate of (R) allethrolone was converted into (S) allethrolone.

EXAMPLE 9

STEP A: hemisuccinate of (R) allethrolone

A solution of 7.36 g of methane sulfonate of (S) allethrolone in 8 ml of hexamethylphosphortriamide was slowly added under an inert atmosphere to a solution of 4.48 g of sodium hemisuccinate in 25 ml of hexamethylphosphortriamide and the mixture was stirred at 25° C for 25 hours and was then poured into water. The pH of the mixture was adjusted to 9.5 with sodium bicarbonate and and the mixture was extracted with petroleum ether (b.p. = 35°–75° C). The organic extracts were evaporated to dryness to obtain 1.258 g of a residue which contained 0.7 g of the succinate of di-(R)-allethrolone.

The combined aqueous phases were extracted with methylene chloride to remove residual hexamethylphosphortriamide and after cooling to 5° C, the pH of the aqueous phase was adjusted to 1. The aqueous phase was extracted with ethyl acetate and the organic extracts were evaporated to dryness. The 4.73 g of residue was taken up in 10 ml of benzene and the mixture was stirred and filtered. The filtrate was evaporated to dryness and the residue was chromatographed over silica gel and was eluted with a 40-60-1 benzene-ethyl acetate-acetic acid mixture to obtain 4.05 g of the hemisuccinate of (R) allethrolone.

STEP B: (R) allethrolone

A mixture of 4.05 g of the product of Step A in 20 ml of aqueous 2N hydrochloric acid was refluxed for 5 hours and was worked up as in Step B of Example 7 to obtain 2.5 g of (R) allethrolone. The succinate of di-(R)-allethrolone was also acid hydrolyzed to obtain (R) allethrolone. By an analogous procedure, methane sulfonate of (R) allethrolone was converted to (S) allethrolone.

Various modifications of the process of the invention may be made without departing from the spirit or scope thereof and it is to be understood that the invention is intended to be limited only as defined in the appended claims.

We claim:

1. A process for the preparation of optically active (S) or (R) allethrolone comprising reacting in at least one organic solvent selected from the group consisting of dimethylformamide, dimethylsulfoxide, dimethoxyethane, acetonitrile, aliphatic ketones, hexamethylphosphortriamide, alkanols and monocyclic aromatic hydrocarbons a sulfonate of optically active allethrolone of (R) or (S) configuration of the formula

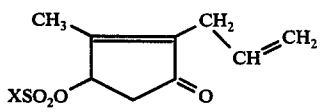

wherein X is selected from the group consisting of alkyl of 1 to 3 carbon atoms and phenyl optionally substituted in the p-position with a member of the group consisting of methyl, chlorine, bromine and fluorine with a salt selected from the group consisting of alkali metal, alkaline earth metal, ammonium and a tertiary base of an organic carboxylic acid selected from the group consisting of aliphatic carboxylic acids of 1 to 6 carbon atoms optionally substituted with one or more halogens and a monocyclic aromatic carboxylic acid to form the ester of the carboxylic acid and (S) or (R) allethrolone antipodal to that of the starting sulfonate of allethrolone and subjecting the latter to acid hydrolysis to form (S) or (R) allethrolone antipodal to the starting sulfonate.

2. The process of claim 1 wherein the acid hydrolysis is effected with a dilute solution of a strong acid.

3. The process of claim 1 wherein the starting sulfonate is a sulfonate of (R) allethrolone.

4. The process of claim 3 wherein the said sulfonate is methane sulfonate or p-toluene sulfonate.

5. The process of claim 1 wherein the starting sulfonate is a mixture of a sulfonate of (R) allethrolone and a sulfonate of (S) allethrolone rich in the sulfonate of (R) allethrolone.

* * * * *